US00PP12296P2

(12) United States Plant Patent
Platt

(10) Patent No.: US PP12,296 P2
(45) Date of Patent: Dec. 18, 2001

(54) SWAMP CYPRESS 'CASCADE FALLS'

(75) Inventor: Graeme Charles Platt, Auckland (NZ)

(73) Assignee: David and Noeline Sampson, New Plymouth (NZ)

( * ) Notice: Subject to any disclaimer, the term of this patent is extended or adjusted under 35 U.S.C. 154(b) by 0 days.

(21) Appl. No.: 09/408,719

(22) Filed: Sep. 29, 1999

(51) Int. Cl.[7] ..... A01H 7/00
(52) U.S. Cl. ..... Plt./213
(58) Field of Search ..... Plt./213

(56) References Cited

PUBLICATIONS

Plant Breeders Rights Certificate, dated Apr. 4, 1999, to New Zealand.
UPOV–ROM GTITM Computer Database 2000/05, GTI JOUVE Retrieval Software.*

* cited by examiner

*Primary Examiner*—Bruce R. Campell
*Assistant Examiner*—A Para
(74) *Attorney, Agent, or Firm*—Klarquist Sparkman, LLP

(57) ABSTRACT

A Swamp Cypress tree named 'Cascade Falls' having weeping branches.

2 Drawing Sheets

DESCRIPTION

The present invention relates to a new and distinct variety of *Taxodium distichum*, Swamp Cypress, which has been given the varietal name 'Cascade Falls'.

I discovered the original tree of my new variety as a seedling growing in a cultivated area along the bank of a small man-made lake on my property in Albany, Auckland, New Zealand. My attention was drawn to this new plant because of its distinct weeping characteristic that is unlike any other Swamp Cypress trees of which I am aware. Subsequently, at my direction, my original tree has been asexually propagated by grafting onto *Taxodium distichum* understock. Branches of my new variety weep downwardly from the graft, thereby confirming that this unique and distinct characteristic of my new variety is firmly fixed. These observations of the original tree and of asexually propagated progeny have confirmed that my new variety represents a new and improved variety of Swamp Cypress as particularly evidenced by a weeping growth habit. Asexual propagation of the new variety by grafting onto *Taxodium distichum* understock has been accomplished in New Plymouth, New Zealand and also in Boring, Oreg.

The accompanying photographs depict the color of the tree and foliage of my new variety as nearly true as is reasonably possible to make the same in a color illustration of this character. It should be noted that colors vary with growing conditions and time of year as well as with lighting conditions at the time the photographs are taken.

Color references are to The R.H.S. Colour Chart, Royal Horticultural Society, London, United Kingdom, unless the context clearly indicates the color term is intended to have its ordinary dictionary meaning.

My 'Cascade Falls' variety of Swamp Cypress tree has not been observed under all growing conditions and, thus, variations may occur as a result of different growing conditions.

Figure 1:
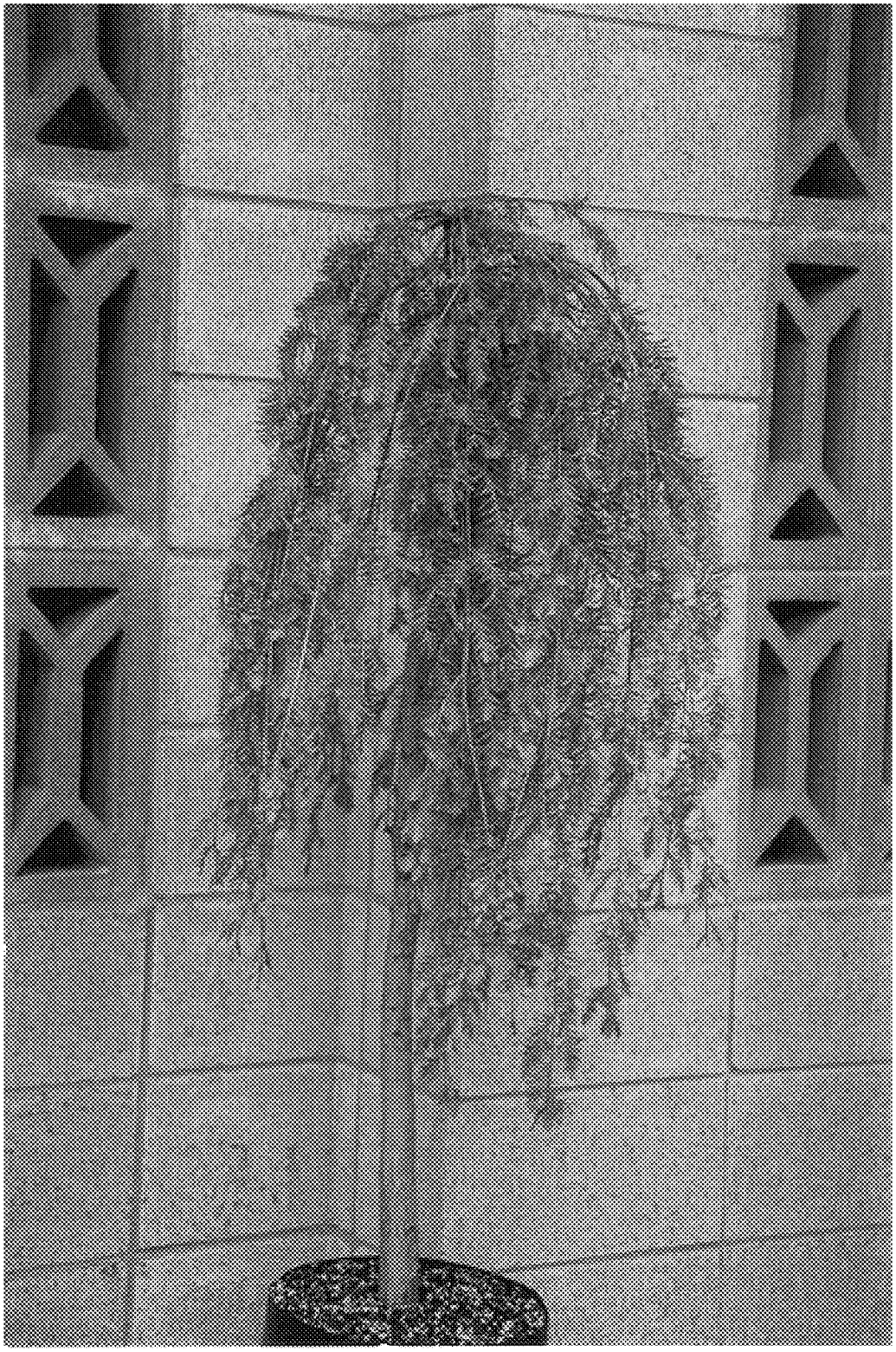
FIG. 1 is a photograph of a tree of my new variety grafted onto *Taxodium distichum* understock.
Figure 2:
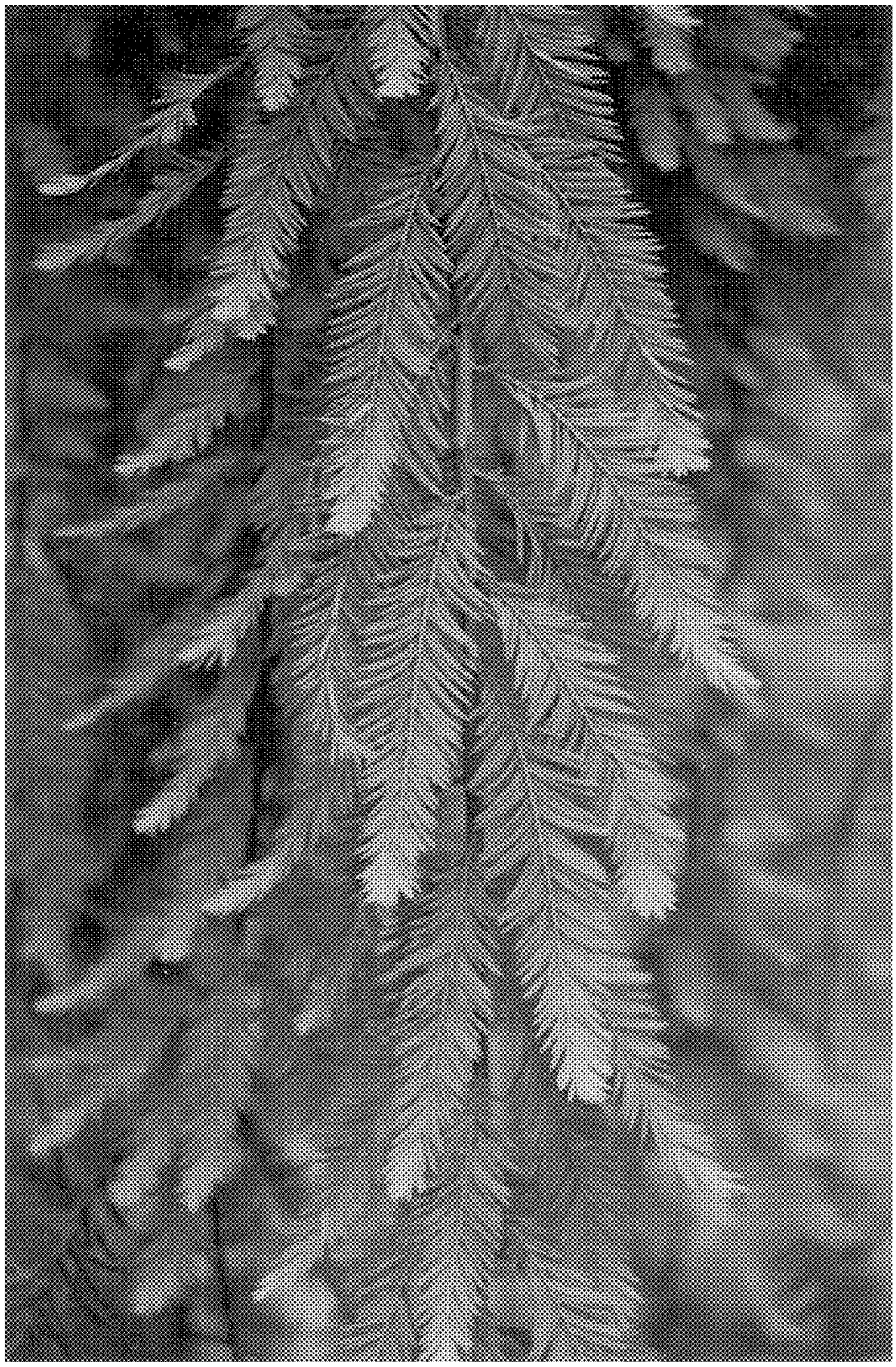
FIG. 2 is a close up photograph of several branches from a tree of my new variety.

My new variety of Swamp Cypress tree is characterized by its long, fine pendulous branches which weep toward the ground. As shown in FIG. 1, these branches curve outwardly from the trunk of the tree and then hang vertically downwardly. In FIG. 1, the graft is supported several feet above the ground by the understock. The branches of the original tree of my new variety also extended downwardly toward the ground. Thus, my new variety of Swamp Cypress tree has a unique growth habit making it highly desirable for landscaping applications.

My new variety has short to medium internode lengths on the main stem. Grafted plants growing in a greenhouse environment in Boring, Oreg., have been observed to have primary branch nodes about 1.25 cm to 3 cm apart on the main stem. Multiple branches often emerge from a single node. My new variety exhibits slow apical growth with the strongest growth occurring from lateral branches. For example, apical growth from about five to eight centimeters per year has been observed. Primary branches have been observed to grow forty centimeters or more in a single growing season. The bark of my new variety on two-year old branches has been observed to be somewhat flakey and of a brown color, like RHS 177B. This same color has been observed for the mature trunk bark. New growth branches are more red-brown in color like RHS 182B although when they first emerge, the branch tips are a yellow-green, like RHS 144A. These colors are believed to be like those of the species.

The tree of my variety has long, primary branches with long secondary branches as well. The secondary branches are irregularly arranged and extend from varying positions from the primary branches. The primary branches extend approximately horizontally on a grafted plant from the grafted stem for the first 4 to 7 cm with the branch then curving downwardly. Thus, the branches exhibit a pendulous or weeping attitude.

The leaves are needle-like, flat and thin, and are arranged in a flat array with the leaves being outspread in two rows from opposite sides of twigs. The leaves alternate along the twigs. The twigs in general are radially arranged on branches. Some individual needles are spirally arranged on new growth branches. The tree is deciduous.

The leaves of my new variety have been observed to have a dark green upper surface like RHS 137A in the summer with the leaves turning red-brown in autumn. Lighter yellow-green coloration has been observed on young growth, like RHS 144A. The undersurface of the leaves in summer have been observed to be like RHS 138A, although this varies with the time of the year. The individual leaves have a length to about 3 cm with a very narrow width.

My variety has been asexually propagated by grafting onto *Taxodium distichum* understock.

The following botanical description in general concerns approximately 16-month old plants observed growing in Boring, Oreg.

THE PLANT

Parentage: Chance Swamp Cypress seedling of unknown origin, growing in a cultivated area in Albany, Auckland, New Zealand.

Tree shape: Original tree has mounted shape due to slow apical growth in combination with weeping branches. When grafted, the branches weep downwardly from the grafted stem. Very weak apical growth with strongest growth occurring from lateral branches. Growth habit tends to be prostrate, unless staked or otherwise supported.

Bark: Flakey, brown colored bark, like RHS 177B when mature; red-brown like RHS 182B when new; initially emerging with a yellow-green color, like RHS 144A.

Branches: Long primary branches and secondary branches. Primary branches when the trees are staked typically measure about 90 to 125 cm (about 3 to 4 feet) long for 16-month old trees growing in Boring, Oreg. In a grafted tree, the primary branches emerge generally hoziontally from the main stem for the first 4–7 cm. with the branches then curving downwardly. Branch arrangements irregular.

Leaves: Needles are 2 ranked, linear, typically about 10 to 20 mm long, and about 1.5 mm wide. Apex is sharply acute with a needle-like point. Base is acute, though slightly less acute than apex, and margin is entire. Needles are scale-like on the persistant shoots, spirally arranged.

Leaf color: Upper leaf surface is dark green like RHS 137A in summer. Undersurface is a brown-green like RHS 138A in the summer. The needles die in the fall and turn a red-brown color before being shed.

Sexual characteristics: No flowers, pollen, cones, or seed have been observed on any plants of my new variety as of this time.

I claim:

1. A new and distinct variety of Swamp Cypress tree substantially as herein shown and described, characterized particularly as to novelty by its weeping branch habit of growth.

* * * * *